US00PP37113P2

(12) United States Plant Patent
Hansen

(10) Patent No.: US PP37,113 P2
(45) Date of Patent: Nov. 25, 2025

(54) ***HOSTA* PLANT NAMED 'Avant Garde'**

(50) Latin Name: ***Hosta* hybrid (Tratt.)**
Varietal Denomination: Avant Garde

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,373

(22) Filed: Dec. 20, 2024

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
CPC ... A01H 5/12; A01H 5/02; A01H 5/00; A01H 6/12
See application file for complete search history.

(56) References Cited

PUBLICATIONS

Hosta Registrar The Hosta Treasury, retrieved on May 13, 2025 at https://www.hostaregistrar.org/, 3 pp. (Year: 2025).*
International Society for Horticultural Science, Taxonomic Listing of genera and families with an ICRA, retrieved on May 13, 2025 at https://www.ishs.org/sci/taxlist/htaxlist.htm, 6 pp. (Year: 2025).*

* cited by examiner

*Primary Examiner* — June Hwu

(57) ABSTRACT

A new and distinct *Hosta* plant named 'Avant Garde' of large arching mounds of broadly ovate leaves having wide bluish-green margins and khaki with olive-green centers. The variegation is also attractively displayed with numerous featherings of intermediate colors between the center the leaf margins. The flowers are very pale lavender held just above the foliage beginning in late June for about three weeks. 'Avant Garde' has excellent large mounded habit and is useful in the landscape, as a specimen, or en masse.

2 Drawing Sheets

Botanical classification: *Hosta* hybrid (Tratt.).
Variety denomination: 'Avant Garde'.

STATEMENT REGARDING PRIOR DISCLOSURES UNDER 37 CFR 1.77(B)(6)

*Hosta* 'Avant Garde' was first introduced by the inventor as a non-enabling description through the International Cultivar Registration Authority registration in early 2024. No plants of *Hosta* 'Avant Garde' have been sold in this country or anywhere in the world, nor has any disclosure of the new plant been made, more than one year prior the filing date of this application.

BACKGROUND AND ORIGIN OF THE PLANT

The present invention relates to a new and distinct *Hosta* plant named *Hosta* 'Avant Garde' hereinafter also referred to as the new plant or by the cultivar name 'Avant Garde'. *Hosta* 'Avant Garde' was hybridized by the inventor on Jun. 25, 2015, at a wholesale perennial nursery in Zeeland, Michigan, USA. The female parent was a proprietary, unreleased, streaked sport of 'Elegans' known only as 14-SP-HOST-3001 (not patented) and the male parent was 'Viking Ship' not patented. The new plant was assigned the breeder code 15-274-2 and passed the initial evaluation in the summer of 2016.

'Avant Garde' has been asexually propagated by division at the same nursery since 2021 and also by careful shoot tip plant tissue culture with the resultant asexually propagated plants having retained all the same traits as the original plant. The new plant is stable and reproduces true to type in successive generations of asexual reproduction.

There are over 7,000 registered and established *Hosta* cultivars with The American *Hosta* Society, which is the International Cultivar Registration Authority for the genus *Hosta*. Several of these have green leaf blades with variegated margins. The most similar *Hosta* cultivars known to the applicant are 'Awakening Spirit' U.S. Plant patent application Ser. No. 18/831,380, 'Beckoning' U.S. Plant Pat. No. 18,371, 'Brother Stefan' (not patented), 'Lean on Me' (not patented), 'Moment to Treasure' U.S. Plant Pat. No. 36,700, 'Seduced' (not patented), and 'Sound of Music' U.S. Plant Pat. No. 35,563.

'Awakening Spirit' has a shorter and more horizontal habit with smaller foliage that is more bullate. 'Beckoning' has larger and more glaucous leaf blades with lighter chartreuse centers, more leaf veins that are more deeply impressed, and taller flower scapes. 'Brother Stefan' has foliage that is slightly smaller, more bullate, with a less acute apex, and scape is shorter with pure white flowers. 'Lean on Me' has larger more glaucous leaves with less yellowish-chartreuse leaf centers. 'Moment to Treasure' has a smaller habit with smaller leaves that display a brighter yellowish center and less bluish-green margin, and the scape is shorter with pale lavender flowers. 'Seduced' has a smaller habit with smaller leaves having a lighter green margin and near white flowers. 'Sound of Music' has larger foliage and larger habit, the leaves are more bullate, and the flowers are light lavender with darker lavender veins.

The female parent has a more bullate foliage that has a streaked variegation pattern with yellowish-chartreuse and bluish-green not confined to the margins or centers. The male parent has a larger more upright habit with larger more glaucous foliage, more rippled margins, without foliar variegation, and the flowers have more lavender coloration.

Other *Hosta* cultivars may have individual traits similar to 'Avant Garde' but the new plant differs from the above listed cultivars and all other *Hostas* known to the applicant by the combination of the following traits.

1. Leaves are large-sized, broadly ovate, with acute apices and cordate base;
2. Arching leaves have bluish-green margin and khaki with olive-green center;
3. Leaf margin is bluish-green and khaki with olive-green center and numerous featherings of intermediate colors between the margin and center;
4. Flowers are very pale lavender, densely arranged on scapes with the first flowers beginning to open just above the foliage;
5. Large mounded habit and useful in the garden as edging or front border, in containers, as a specimen or en masse.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings show an eight-year-old 'Avant Garde' plant in a trial garden at a nursery in Zeeland, MI with supplement fertilizer and water as needed.

DETAILED BOTANICAL DESCRIPTION

Figure 1:
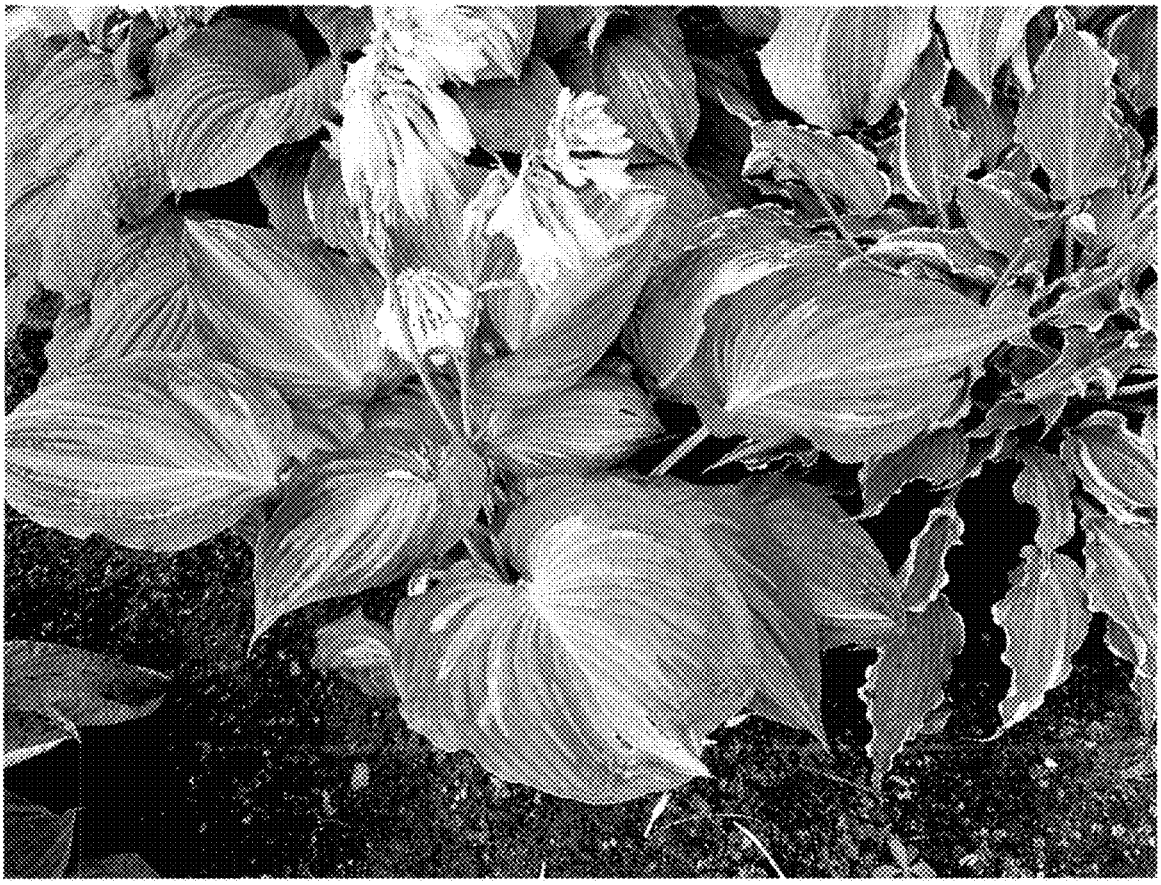
FIG. 1 shows the landscape foliage habit of a new plant at early flowering.
Figure 2:
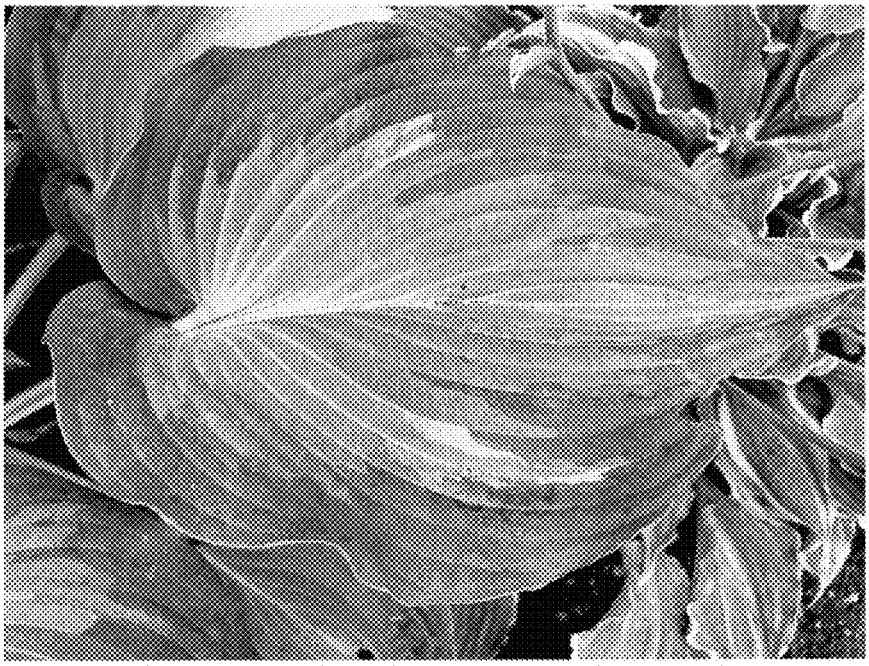
FIG. 2 shows a close-up of a leaf.
Figure 3:
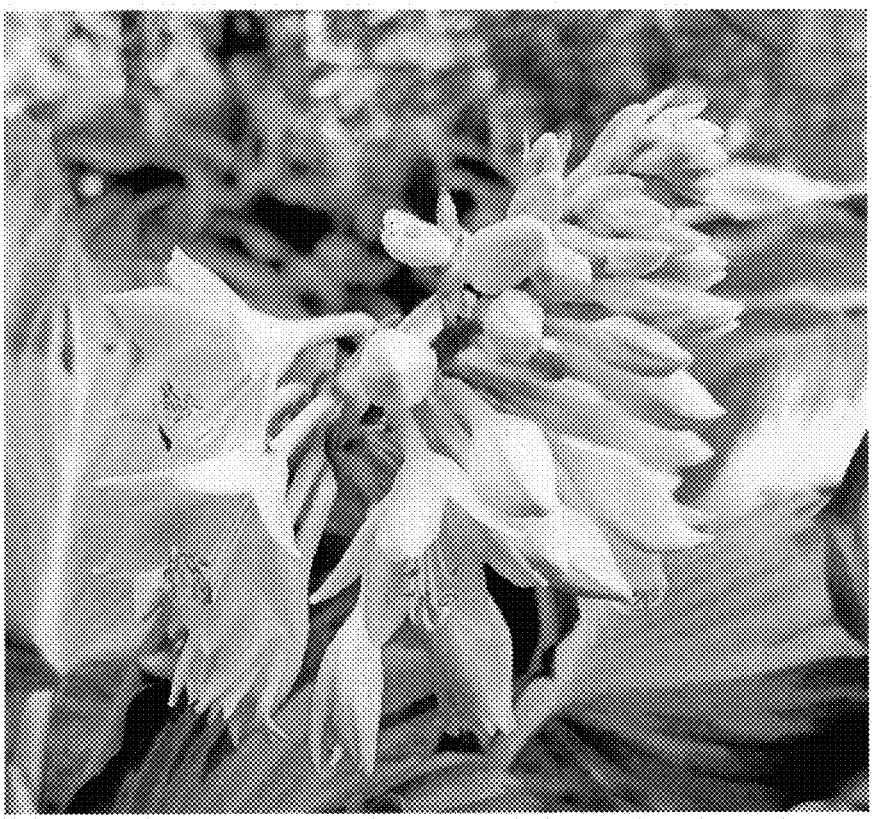
FIG. 3 shows a close-up of the flower scape with bracts flowers and buds.

The following descriptions and color references are based on the 2015 edition of The Royal Horticultural Society Colour Chart except where common dictionary terms are used. The new plant, *Hosta* 'Avant Garde', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of an eight-year-old plant in a shaded trial garden in Zeeland, Michigan with supplemental water and fertilizer.

Botanical classification: *Hosta* hybrid;

Parentage: Female or seed parent the proprietary streaked sport of 'Elegans'; male or pollen. parent 'Viking Ship';

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a large mound of arching petioles, and leaves, and erect scapes flowering above foliage;

Emerging shoot color: Green;

Plant size: Foliage height to about 56 cm above soil line to the top of the leaves, to about 79 cm tall to the top of the flowers, and to about 91 cm wide at the widest point slightly above soil line;

Foliage description: Broadly ovate; acute apex, cordate base; slightly undulate, entire; glabrous and lightly glaucous both surfaces; flexible; not bullate; twisting absent;

Leaf blade size: To about 30.5 cm long and about 25.5 cm wide near middle; margin width 2.5 cm to 6.4 cm wide, average 3.5 cm wide;

Leaf blade color: Early season and expanding adaxial margin nearest RHS 137B, adaxial center nearest RHS 146C, adaxial colors in the intermediate region between center and margin comprising RHS 138B, and RHS 144A; early season and expanding abaxial margin between RHS N138B and RHS 137B, abaxial center nearest RHS 146D, intermediate region comprising nearest RHS N138C and between RHS 146C and RHS 147C; mid-season and later adaxial margins nearest RHS 137A, center between RHS 146D and RHS N144D and lightening toward autumn in higher light to between RHS 146C and RHS 20C, adaxial intermediate region comprising: RHS 144A, RHS 147C, and between RHS N144A and RHS 146D, with a thin line of between RHS 160B and RHS 151D outlining the center in some random regions; mid-season and later abaxial margin nearest RHS 137B, center between RHS N144A and RHS 146D, intermediate region comprising: nearest RHS 146C, between RHS 146C and RHS 147C, and RHS 191B;

Petiole: Glabrous, slightly glaucous becoming slightly lustrous adaxial and glabrous and slightly glaucous abaxial; deeply concavo-convex; stiff; to about 34 cm long and 11 mm wide at base and about 6 mm deep;

Petiole color: Adaxial margins about 1 mm wide nearest RHS 137A, center between RHS 1D and RHS 4D; abaxial margins about 1 mm wide nearest RHS 137A;

Veins: Fourteen to sixteen pairs and midrib; parallel; lightly impressed adaxial; costate and rough abaxial;

Veins color: Adaxial nearest RHS 160D in center and nearest RHS 137A along margin, abaxial nearest RHS 18C;

Flower description:

Buds one to two days prior to opening: Clavate with rounded apex and narrow tube base; about 39 mm long and 12 mm in diameter at the bulb with base narrowing in basal 15 mm to about 3 mm diameter;

Bud color: Nearest RHS NN155D with a faint blush of nearest RHS 84D distally in the bulb portion and nearest RHS 145D proximally in the tube portion;

Flowers: Perfect; flared campanulate; outwardly; to 49 mm long to exserted stigma; corolla fused in basal 35 mm, free in the distal 20 mm and fused in the proximal 28 mm, about 48 mm long and 25 mm wide at tepal apices; corolla tube portion 20 mm long and 3 mm diameter; flower size decreasing distally;

Flower lasting: Persists for a normal period, usually about one day on plant; mostly secund; flowers tightly arranged on scape;

Flowering period: Scapes remain effective with flowers beginning mid-June for about three to four weeks;

Flower number: About 52 flowers per scape;

Fragrance: No detectable fragrance;

Tepal: Two sets of three; clavate with broadly acute apex; entire margin; glabrous; entire margins; about 48 mm long; outer set to about 10 mm wide, inner set to about 9 mm wide slightly above fusion point; fused in basal 28 mm; basal 18 mm constricted into tube;

Tepal color: Adaxial blade nearest RHS NN155D along edges with faint blush of between RHS 76C and RHS 84D in center 5 mm to 6 mm, inner corolla tube nearest RHS NN155D; abaxial blade nearest RHS NN155D along edges and between RHS 84D and RHS NN155C in the center one half, abaxial outer corolla tube between RHS NN155D and RHS 157D;

Gynoecium: Single; 51 mm long; superior;

*Style*.—Cylindrical; about 44 mm long, 1 mm diameter; curved upward 90 degrees in distal 10 mm; color between RHS 145D and RHS NN155D distally and nearest RHS 145C proximally.

*Stigma*.—Puberulent; tri-lobed; about 1 mm across and 1 mm tall; color nearest RHS NN155A.

*Ovary*.—Ellipsoidal; superior; apex rounded; base rounded to truncate; moderately fluted; to about 6 mm long and 3 mm diameter in middle; color nearest RHS 145A.

Androecium: Six;

*Filaments*.—Six; cylindrical; glabrous; slightly lustrous; approximately 48 mm long and 0.5 mm in diameter; curved upward to about 90 degrees in the distal 10 mm; color between RHS 145D and RHS NN155D distally and nearest RHS 145C proximally.

*Anthers*.—Ellipsoidal, with rounded ends; basifixed, longitudinally dehiscent; about 4 mm long and 1.5 mm wide; color nearest RHS 161B with a central adaxial line nearest RHS 20A.

*Pollen*.—Spherical; less than 0.1 mm long; abundant; color nearest RHS 17A.

Peduncle: Cylindrical; usually one per mature division; about ten per plant; glabrous; glaucous; mostly erect; to about 78 cm tall, and about 10 mm in diameter at base;

Inflorescence: Flowering portion about 16 cm long and 14 cm wide;

Peduncle color: Between RHS 158A and RHS 158B;

Pedicel: Cylindrical; glabrous; glaucous; about 13 mm long and 1.5 mm diameter; outwardly;

Pedicel color: Between RHS 145C and RHS 145B;

Floral bracts: Each flower normally subtended by a single bract; ovate; acute apex and truncate base; entire margin; glabrous and glaucous abaxial and adaxial; to about 28 cm long 8 mm wide, decreasing distally;

Floral bract color: At time of flowering adaxial and abaxial proximal 1 mm wide margin and distal one-half nearest RHS 146D and central 6 mm nearest RHS 155D with a light blush of nearest RHS 59A;

Fruit: Tri-valved dehiscent capsule; ellipsoidal to cylindrical with apex apiculate and attenuate base; about 35 mm long and 8 mm diameter;

Fruit color: Between RHS 158B and RHS 160D with a slight blush of nearest RHS 59B as maturing, RHS 161D when ripe;

Seed: Typically, about 21 to 36 per capsule with open pollination; endospermic; flattened-ellipsoidal wing surrounding embryo at one end of ellipse; to about 11 mm long, 3 mm wide and 1.5 mm thick at embryo;

Seed color: Between RHS 200A and RHS 202A;

Plant growth: The new plant grows best and shows best coloration with plenty of moisture, adequate drainage and light shade, but is able to tolerate some drought when mature.

Hardiness: Winter hardy from at least from USDA zone 3 through 8;

Pest and disease resistance: Resistance or susceptibility to pests (including: *Odocoileus virginianus* and *Oryctotagus cuniculus*) and diseases common to *Hostas* is equal that typical of other cultivars.

It is claimed:

1. A new and distinct *Hosta* plant named 'Avant Garde' as herein described and illustrated.

* * * * *